(12) United States Patent
Tretheway et al.

(10) Patent No.: US 11,559,425 B2
(45) Date of Patent: Jan. 24, 2023

(54) OSTOMY APPLIANCE

(71) Applicant: SALTS HEALTHCARE LIMITED, Birmigham (GB)

(72) Inventors: Lee Tretheway, Birmingham (GB); Marcus Allen, Birmingham (GB); Iain Powner, Birmingham (GB); Jesus Alfaro, Birmingham (GB); Kieran Williams, Birmingham (GB)

(73) Assignee: Salts Healthcare Limited, Birmingham (GB)

( * ) Notice: Subject to any disclaimer, the term of this patent is extended or adjusted under 35 U.S.C. 154(b) by 265 days.

(21) Appl. No.: 16/648,491

(22) PCT Filed: Sep. 21, 2018

(86) PCT No.: PCT/GB2018/052692
§ 371 (c)(1),
(2) Date: Mar. 18, 2020

(87) PCT Pub. No.: WO2019/058128
PCT Pub. Date: Mar. 28, 2019

(65) Prior Publication Data
US 2020/0276044 A1    Sep. 3, 2020

(30) Foreign Application Priority Data
Sep. 22, 2017 (GB) .................................. 1715395

(51) Int. Cl.
*A61F 5/441*    (2006.01)
*A61F 5/445*    (2006.01)

(52) U.S. Cl.
CPC .............. *A61F 5/441* (2013.01); *A61F 5/445* (2013.01)

(58) Field of Classification Search
CPC ...... A61F 5/445; A61F 5/4404; A61F 5/4405; A61F 5/441
See application file for complete search history.

(56) References Cited

U.S. PATENT DOCUMENTS 4,084,590 A * 4/1978 Caraway ................. A61F 5/445
604/350
4,411,659 A * 10/1983 Jensen .................... A61F 5/441
604/340

(Continued)

FOREIGN PATENT DOCUMENTS

EP    0 868 892 A1    10/1998
EP      0868892 A1 * 10/1998 ............. A61F 5/445

(Continued)

OTHER PUBLICATIONS

Search Report Under Section 17(6) dated May 9, 2018, in Application No. GB1715395.8, 2 pages.

(Continued)

*Primary Examiner* — Guy K Townsend
(74) *Attorney, Agent, or Firm* — Polsinelli PC

(57) ABSTRACT

An ostomy appliance including:
  first and second walls connected to each other at or near their peripheries, the first wall having a stoma-receiving opening;
  a connection member connected to the first wall for attaching the appliance to a user;
  a waste collecting chamber defined by the first and second walls for receiving waste and/or gas from the stoma-receiving opening;
  a further chamber defined by at least third and fourth walls which are connected to each other;
  a gas opening provided in either or both of the third or fourth walls for permitting waste gases to pass therethrough from the waste collecting chamber;

(Continued)

a gas vent for permitting gases in the further chamber to escape to atmosphere; and wherein movement of the first and second walls away from each other, from waste or gases entering the waste collecting chamber, increases or at least maintains the volume of the further chamber.

23 Claims, 5 Drawing Sheets

(56) References Cited

U.S. PATENT DOCUMENTS

| | | | | |
|---|---|---|---|---|
| 4,519,797 A * | 5/1985 | Hall | A61F 5/445 | 604/339 |
| 4,604,095 A * | 8/1986 | Samuelsen | A61F 5/4405 | 604/350 |
| 4,917,689 A * | 4/1990 | Coombes | A61F 5/445 | 604/338 |
| 5,009,648 A * | 4/1991 | Aronoff | B32B 27/08 | 604/338 |
| 5,250,042 A * | 10/1993 | Torgalkar | A61F 5/441 | 604/339 |
| 5,468,235 A * | 11/1995 | La Gro | A61F 5/441 | 604/333 |
| 5,549,587 A * | 8/1996 | Norton | A61F 5/441 | 604/340 |
| 5,591,144 A * | 1/1997 | Smith | A61F 5/445 | 604/327 |
| 5,690,622 A * | 11/1997 | Smith | A61F 5/441 | 604/327 |
| 5,690,623 A * | 11/1997 | Lenz | A61F 5/441 | 604/332 |
| 5,865,819 A * | 2/1999 | Cisko, Jr. | A61F 5/445 | 604/338 |
| 6,171,288 B1 * | 1/2001 | Wiltshire | A61F 5/441 | 604/333 |
| 6,506,184 B1 * | 1/2003 | Villefrance | A61F 5/441 | 604/333 |
| 6,659,988 B1 * | 12/2003 | Steer | A61F 5/441 | 604/335 |
| 6,709,421 B1 * | 3/2004 | Falconer | A61F 5/445 | 604/335 |
| 6,712,800 B2 * | 3/2004 | Kanbara | A61F 5/441 | 604/333 |
| 6,773,420 B2 * | 8/2004 | Kanbara | A61F 5/441 | 604/333 |
| 7,476,220 B2 * | 1/2009 | Lillegaard | A61F 5/4405 | 604/338 |
| 9,119,727 B2 * | 9/2015 | Hannan | A61F 5/445 | |
| 9,549,839 B2 * | 1/2017 | Schertiger | A61F 5/445 | |
| 9,962,282 B2 * | 5/2018 | Chang | A61F 5/445 | |
| 2003/0014023 A1 * | 1/2003 | Kanbara | A61F 5/441 | 604/333 |
| 2004/0059306 A1 * | 3/2004 | Tsal | A61F 5/4404 | 604/332 |
| 2009/0163883 A1 * | 6/2009 | Christensen | A61F 5/441 | 604/328 |
| 2010/0010460 A1 * | 1/2010 | Butler | A61F 5/441 | 604/333 |
| 2010/0145291 A1 * | 6/2010 | Kambara | A61F 13/8405 | 604/333 |
| 2011/0196323 A1 * | 8/2011 | Gill | A61F 5/4405 | 604/333 |
| 2012/0283678 A1 * | 11/2012 | Nguyen-DeMary | A61F 5/445 | 604/338 |
| 2014/0194843 A1 * | 7/2014 | Masters | A61F 5/441 | 604/332 |
| 2015/0320585 A1 * | 11/2015 | Fattman | A61F 5/4407 | 604/344 |

FOREIGN PATENT DOCUMENTS

| | | | | |
|---|---|---|---|---|
| EP | 1 022 002 A1 | 7/2000 | | |
| GB | 2 426 197 A | 11/2006 | | |
| GB | 2 461 721 A | 1/2010 | | |
| GB | 2461721 A * | 1/2010 | | A61F 5/441 |
| GB | 2484978 A * | 5/2012 | | A61F 5/441 |
| GB | 2512655 A | 10/2014 | | |

OTHER PUBLICATIONS

International Search Report dated Mar. 19, 2019, in International Application No. PCT/GB2018/052692, 6 pages.
Written Opinion of the International Searching Authority dated Mar. 19, 2019, in International Application No. PCT/GB2018/052692, 10 pages.

* cited by examiner

OSTOMY APPLIANCE

DESCRIPTION OF INVENTION

This invention relates to an ostomy appliance for collecting human waste. It should be understood that the invention can be utilised in drainable and non-drainable ostomy appliances.

It is known to provide an ostomy appliance ('bag' or 'pouch' as they are commonly known in the art) with one or more intermediate walls to provide a tortuous path for gas to exit the ostomy appliance through a gas vent. Such tortuous paths are created to prevent or at least inhibit a filter, covering a gas vent, from becoming blocked with waste in a waste collecting cavity. In some prior art ostomy appliances such intermediate walls are provided directly opposite a stoma receiving opening, meaning that they can come into direct contact with bodily waste entering the ostomy appliance. Despite intermediate walls working reasonably effectively to prevent bodily waste from reaching the end of the tortuous path and making direct contact with (and blocking) a filter, they often allow bodily waste to travel part way through the tortuous path, for example in between the intermediate walls. This then ensures that those walls stick together thus preventing gas from escaping (even if the filter itself is not directly covered in waste/liquid. As gas pressure increases in the waste collecting cavity, this further exacerbates the problem, because the walls which are already stuck together are pressed further into contact by the gas pressure in the main cavity.

When bodily waste (in the form of solid or liquid) passes through and is trapped between intermediate walls, the intermediate walls can stick together which is referred to as 'pancaking'. When pancaking occurs in an ostomy appliance, there is an extremely limited or no path for waste gas to exit the ostomy appliance which leads to the further problem of ballooning. Ballooning as a direct result of pancaking occurs when gas inside the ostomy appliance inflates the ostomy appliance without escaping. At this point, a user will typically have to replace their ostomy appliance.

It is an object of the present invention to provide an ostomy appliance which addresses these problems.

According to a first aspect of the invention, we provide an ostomy appliance including:
 first and second walls connected to each other at or near their peripheries, the first wall having a stoma-receiving opening;
 a connection member connected to the first wall for attaching the appliance to a user;
 a waste collecting chamber defined by the first and second walls for receiving waste and/or gas from the stoma-receiving opening;
 a further chamber defined by at least third and fourth walls which are connected to each other;
 a gas opening provided in either or both of the third or fourth walls for permitting waste gases to pass therethrough from the waste collecting chamber;
 a gas vent for permitting gases in the further chamber to escape to atmosphere; and
 wherein movement of the first and second walls away from each other, as a result of waste or gases entering the waste collecting chamber, increases or at least maintains the volume of the further chamber.

According to a second aspect of the invention, we provide an ostomy appliance including:
 first and second walls connected to each other at or near their peripheries, the first wall having a stoma-receiving opening;
 a connection member connected to the first wall for attaching the appliance to a user;
 a waste collecting chamber defined by the first and second walls for receiving waste and/or gas from the stoma-receiving opening;
 a further chamber defined by at least third and fourth walls which are connected to each other;
 a gas opening provided in either or both of the third or fourth walls for permitting waste gases to pass therethrough from the waste collecting chamber;
 a gas vent for permitting gases in the further chamber to escape to atmosphere; and
 wherein movement of the first and second walls away from each other, as a result of waste or gases entering the waste collecting chamber, effects movement of the third and fourth walls away from each other.

According to a third aspect of the invention, we provide an ostomy appliance including:
 first and second walls connected to each other at or near their peripheries, the first wall having a stoma-receiving opening;
 a connection member connected to the first wall for attaching the appliance to a user;
 a waste collecting chamber defined by the first and second walls for receiving waste and/or gas from the stoma-receiving opening;
 a further chamber defined by at least third and fourth walls which are connected to each other;
 a gas opening provided in either or both of the third or fourth walls for permitting waste gases to pass therethrough from the waste collecting chamber;
 a gas vent for permitting gases in the further chamber to escape to atmosphere;
 a drainage outlet in fluid communication with the further chamber for providing a passage for fluid to fall under gravity to the waste collecting chamber; and
 wherein the drainage outlet extends to one side of the stoma receiving opening and downwardly towards a bottom of the appliance.

Further features of the first, second and third aspects of the invention are set out in claims 3 to 17 and 19 to 27 appended hereto.

Embodiments of the invention will now be described by way of example only with reference to the accompanying drawings, of which:—

Figure 1:
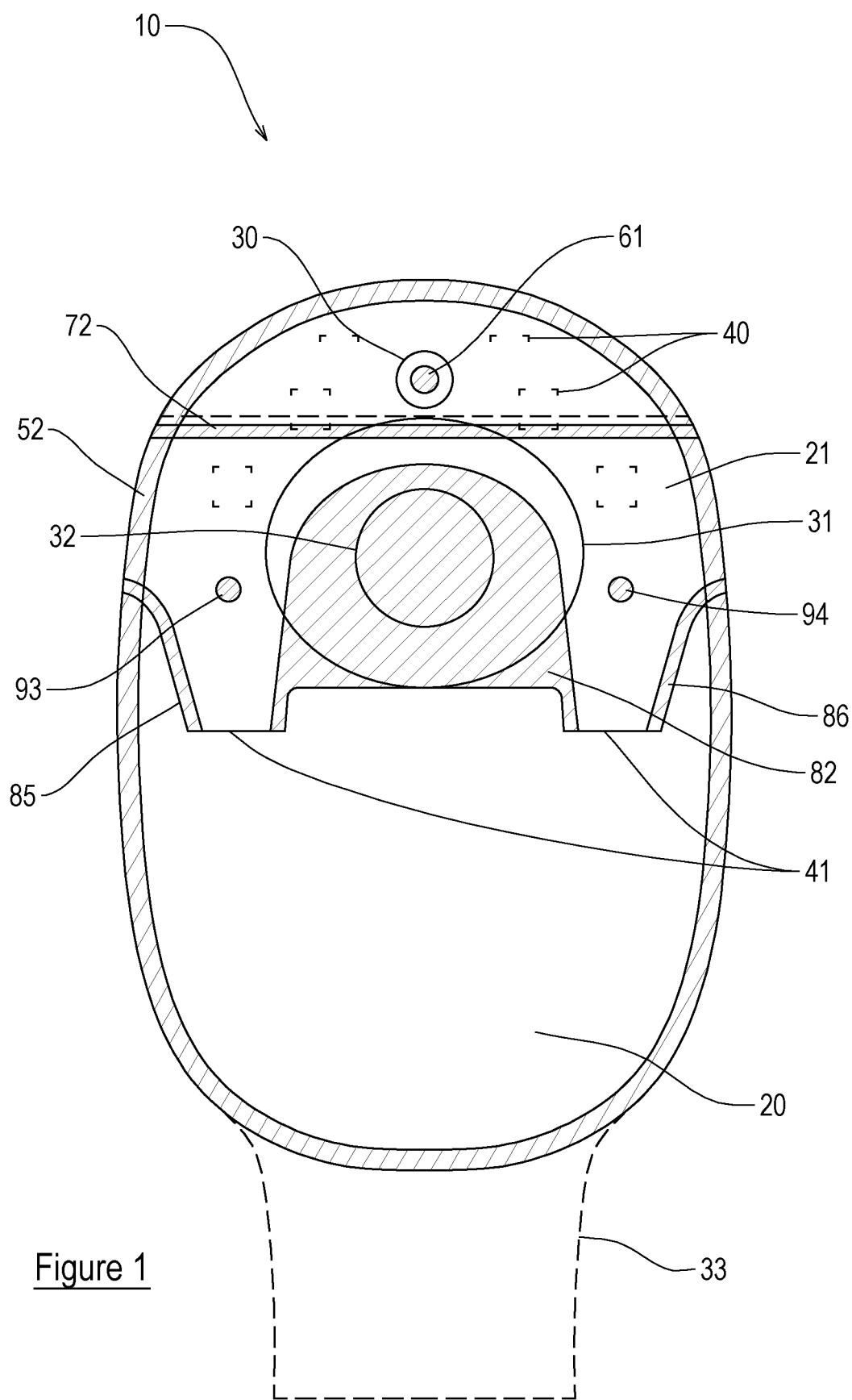
FIG. 1 is a front view of a first embodiment of an ostomy appliance according to the present invention.
Figure 2:
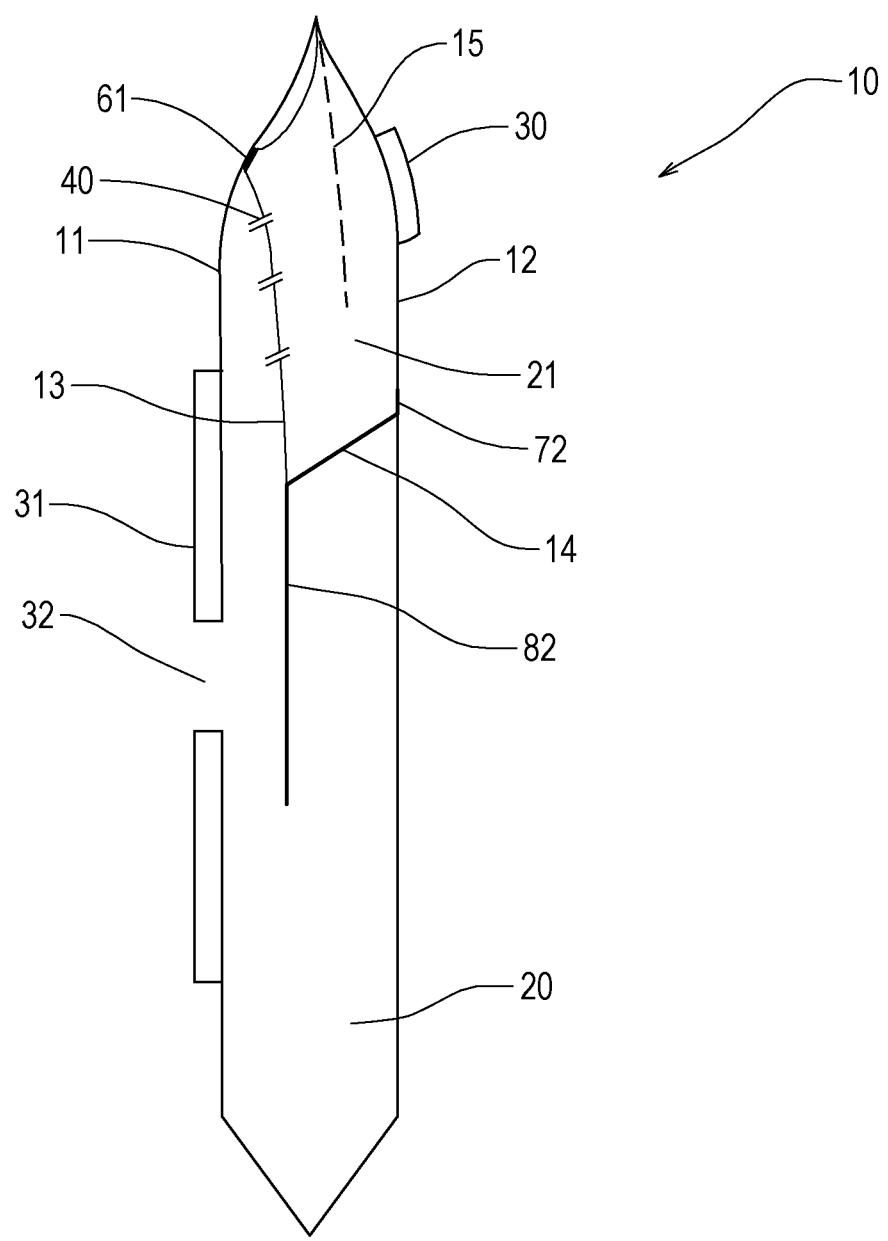
FIG. 2 is a cross-sectional view of the appliance of FIG. 1.
Figure 4:
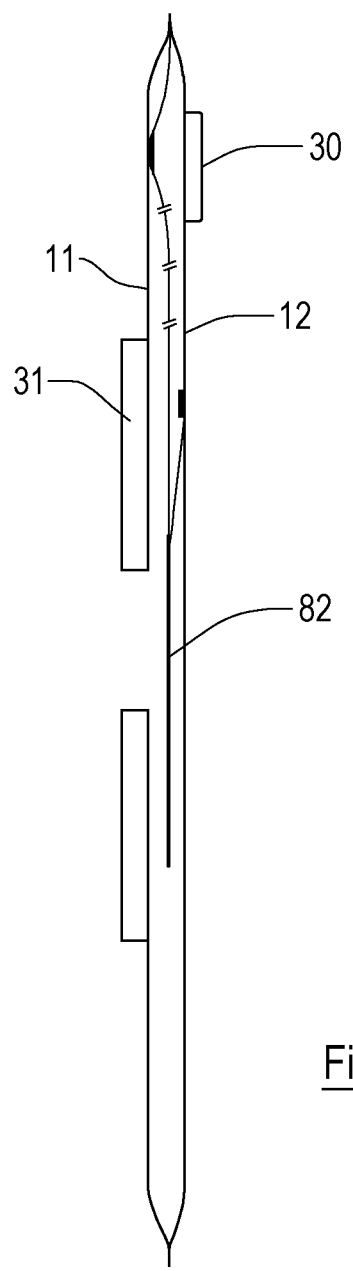
Figure 5:
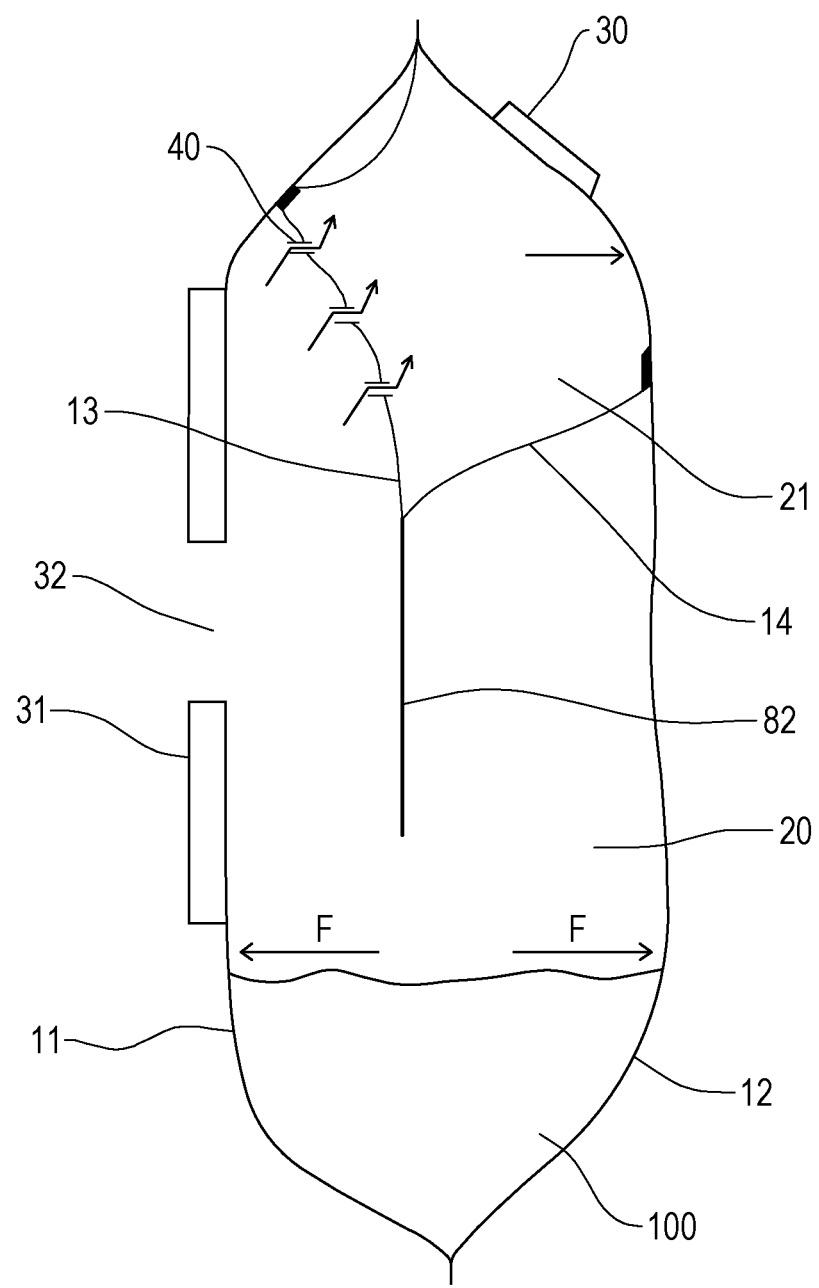

FIG. 4 is a side cross-sectional view of the appliance of FIG. 1 in a deflated condition; and FIG. 5 is a side cross-sectional view of the appliance of FIG. 1 in an inflated condition Referring firstly to FIGS. 1 and 2 these show an ostomy appliance in accordance with the present invention, generally at 10. The general construction of the ostomy appliance 10 is similar to those well known in the art in the sense that it includes a pair of outermost walls, first 11 and second 12, which are connected to each other at or near their peripheries, 51 and 52 respectively, for example by heat welding or using an adhesive. The ostomy appliance shown is a closed appliance, meaning that its contents cannot be emptied, but it should be appreciated that the invention also relates to drainable ostomy appliances such as those having an outlet (shown in broken lines at 33 in FIG. 1, by way of example). Whilst not shown, the appliance 10 may include further external walls to provide more skin comfort to a user, and to conceal some or all of any waste in the appliance 10.

The first wall 11 has a stoma-receiving opening 32 and is connected to a generally circular connection member 31 in the form of a flange for adhering the appliance 10 to a user around their stoma. The connection member 14 could be any appropriate shape, however.

The ostomy appliance 10 as can be seen from FIG. 2, defines a number of chambers therein. A waste collecting chamber 20 is defined between the first 11 and second 12 walls and communicates with the stoma-receiving opening 32 and, in the case when the appliance is a drainable ostomy appliance, the outlet 33. The waste collecting chamber 20 is provided as the primary chamber for receiving bodily waste and/or gas from the stoma-receiving opening 32. A further chamber 21 is defined, in part, by third 13 and fourth 14 walls. The further chamber 21 is positioned above the waste collecting chamber 20 when the ostomy appliance 10 is in use.

Figure 3:
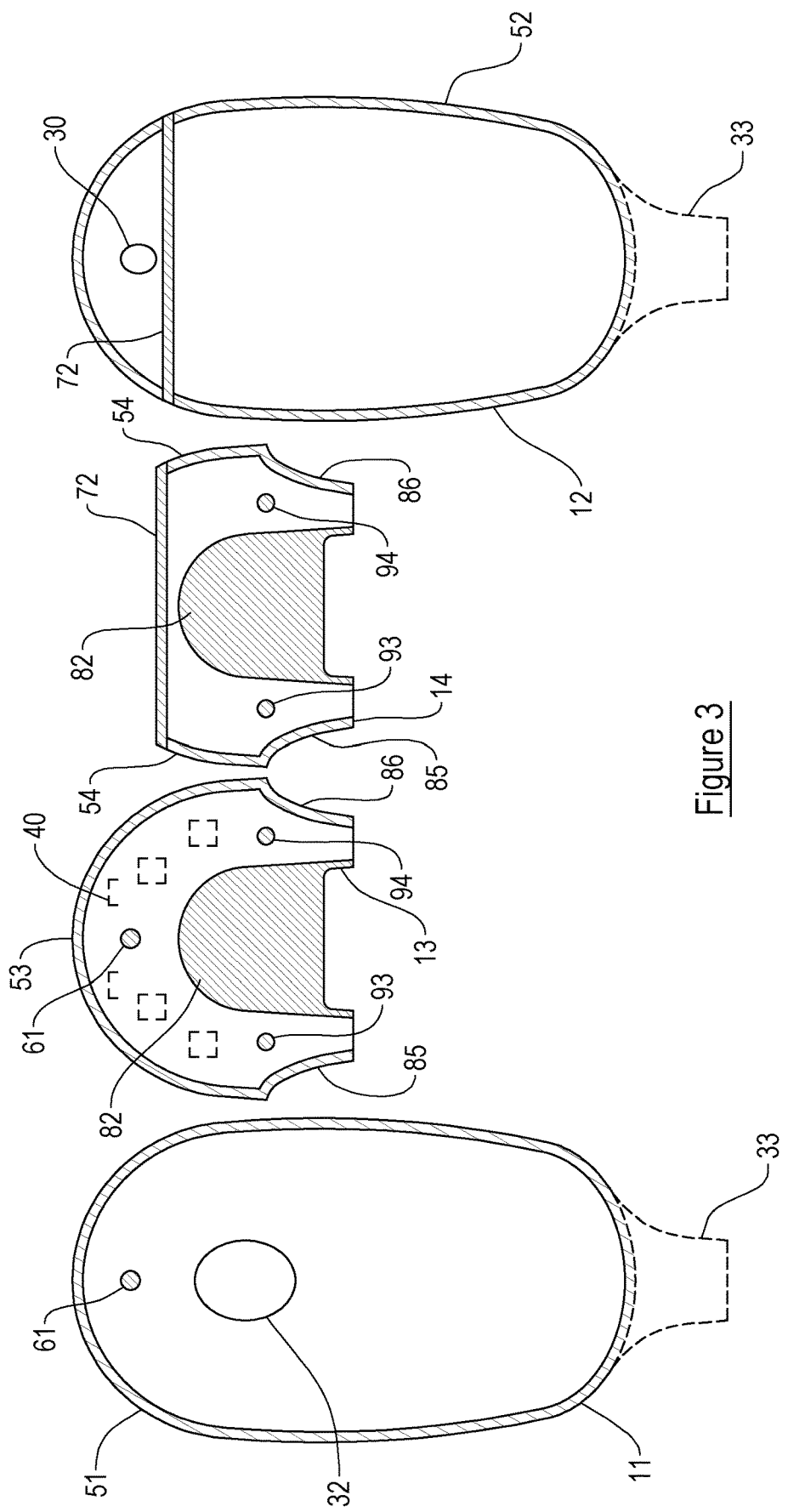
FIG. 3 is an exploded view showing various components parts of the appliance of FIG. 1.

The third 13 and fourth 14 walls are positioned in between the first 11 and second 12 walls as shown more clearly by the exploded view of the ostomy appliance in FIG. 3. The order of the walls is as follows: first wall 11, third wall 13, fourth wall 14 and second wall 12. In the present embodiment, the third 13 and fourth 14 walls are therefore sandwiched in between the first 11 and second 12 walls and there are some portions of the peripheral connection/weld which are share between a number of the walls. Essentially, though, the third 13 and fourth 14 walls are connected at or near their upper ends to the first 11 and/or second 12 walls, with lower portions of the walls 13, 14 extending downwardly between the walls 11, 12 towards the bottom of the appliance 10. The connections are preferably carried out by way of heat welding but any known method of connecting walls could be utilised, for example an adhesive could be used.

The layering/welding connections of the walls of the appliance 10 are as follows. The outer peripheries 51, 52 of the first 11 and second 12 walls are welded to each other generally around whole periphery of the first 11 and second 12 walls (save at the outlet 33 if one exists). The third wall 13 has an arcuate upper periphery 53 which is sandwiched between the respective upper peripheries of the walls 11, 12 before welding all three walls together. The fourth wall 14 is connected to the second wall 12 by a weld 72 which extends laterally across the walls 12, 14, just below the filter 30. The linear weld 72 connects at its ends to the peripheral weld which joins the first and second walls 11, 12 to each other.

The third 13 and fourth 14 walls are also connected to each other in a number of locations. Firstly, the third 13 and fourth 14 walls are welded together over a relatively central area 82 which is positioned over the stoma receiving opening 32. The central welded portion 82 permits a user to view the stoma through the walls 13, 14 during use, which is advantageous. The area 82 has an upper portion which is semi-circular and a lower portion which is substantially trapezoidal. Thus, it is shaped substantially as the silhouette of a dome. At each side of the appliance 10, e.g. at each side of the area 82, the third 13 and fourth 14, walls are connected to each other by respective weld lines 85 (to the left) and 86 (to the right). The welds 85, 86 are each curved and extend downwardly towards the bottom of the appliance and inwardly away from the peripheral weld between the first and second walls 11, 12.

In addition to the elongate or linear welds between the walls, there are also further welds, which in this example are spot welds. The term spot weld is intended to mean that walls are welded to each other over a small area, which is typically circular. It should be appreciated that connections could be provided by other means, and if welding is desired, the area of the weld might be any other appropriate form.

There is a first spot weld 61 which connects the first wall 11 to the third wall 13. The spot weld 61 is located generally centrally of the lateral sides of the appliance 10 and a short distance below the upper periphery of the appliance 10.

Two further spot welds 93 and 94 are provided, which connect the third 13 and fourth 14 walls to each other. Those spot welds 93, 94 are positioned one at either side of the weld area 82 and generally slightly lower than a centre of the stoma receiving opening 32.

The further chamber 21 in this embodiment is therefore defined as the space enclosed between the peripheral weld at the upper part 53 of the third walls, the area weld 82, the welds 85 and 86 and the weld 72.

The further chamber 21, unlike the waste collecting chamber 20, is not provided for waste collection, but rather acts as a gas passage for waste gases to exit the ostomy appliance 10 to atmosphere. To provide this gas passage, at least one gas opening 40 is provided in the third wall 13. The gas opening 40 permits waste gases within the waste collecting chamber 20 to pass through the third wall 13 and into the further chamber 21. Preferably there is a plurality of gas openings 40, although there could be one. In this example the openings 40 are in the form of right-angle slits provided in the third wall 13. The gas openings 40 could be provided as a plurality of perforations in the third wall 13. Despite the figures showing the gas opening 40 as being provided on the third wall 13, the gas opening(s) 40 may in addition or instead be provided on the fourth wall 14.

A gas vent, e.g. an aperture, is provided in the second wall 12 for permitting gases in the further chamber 21 to escape to atmosphere. The gas vent is covered by a filter 30 as shown in FIGS. 1 and 2. In an alternative embodiment, the gas vent may be provided in the first wall 11 to permit waste gases to exit the ostomy appliance 10. In such a configuration, the gas vent should communicate directly with the chamber 21, so that gases in the waste collecting chamber 20 have to pass through the chamber 21 and then to the gas vent.

In some embodiments, a fifth wall 15 may be provided within the further chamber 21 positioned in between the third 13 and fourth 14 and/or second 12 walls in order to divide the further chamber 21 into two sub-chambers. The fifth wall 15 preferably at least partially covers the gas vent and provides a tortuous path within the further chamber 21 for waste gas to escape to atmosphere.

The ostomy appliance 10 is configured such that when waste and/or gases enter the waste collecting chamber 20 from the stoma-receiving opening 32, the first 11 and second 12 walls are caused move away from each other. This is shown by the difference between FIGS. 4 and 5. In FIG. 4 little or no bodily waste and/or gas is inside the waste collecting chamber 20 (e.g. it is deflated) whereas in FIG. 5 bodily waste 100 and/or gas has been introduced into the waste collecting chamber 20 which expands and inflates the chamber 20, thus moving the walls 11, 12 away from each other (other than at their regions of connection, of course). The arrows F at the bottom of the ostomy appliance 10 in FIG. 5 show how the first 11 and second 12 walls of the ostomy appliance 10 move away from each other when waste and/or gas is introduced into the waste collecting chamber 20.

The movement of the first 11 and second 12 walls away from each other in turn, due to the weld 61 between the third 13 and first 11 walls and the weld 72 between the fourth 14 and second 12 walls, ensures that the third 13 and fourth 14 walls also move away from each other (other than at their regions of connection, of course). Therefore, the movement of the first 11 and second 12 walls away from each other, as a result of waste and/or gases entering the waste collecting chamber 20, effects movement of the third 13 and fourth 14 walls away from each other, thus increasing or at least maintaining the volume of the further chamber 21.

This increase in volume is beneficial for a user of the ostomy appliance 10 as it prevents or at least inhibits the walls 12, 13, 14 that define the further chamber 21 from sticking together, if bodily waste/liquid has inadvertently entered the further chamber 21. By ensuring that the defining walls of the further chamber 21 are kept apart or move away from each other when waste and/or gas enters the waste collecting chamber 20, gas is permitted to pass from the waste collecting chamber 20 through a gas openings 40 and into the further chamber 21 where it can then escape the ostomy appliance 10 to atmosphere through the gas vent and filter 30. Thus, the present invention actively maintains an open path for waste gases to follow to atmosphere.

Whilst it is not intended for any waste to flow from the waste collecting chamber 20 into the further chamber 21, it is sometimes the case that a small amount of liquid waste may flow through the gas openings 40 provided in the third wall 13 when, for example, a user lies down to sleep. Advantageously, any of the waste which does inadvertently enter the further chamber 21 will fall under gravity to the waste collecting chamber 20 through advantageously positioned drainage outlets 41.

The present invention includes two such drainage outlets 41, one to each side of the appliance 10, which are defined by continuations of the walls 13, 14 towards the bottom of the appliance 10. Each drainage outlet 41 extends to one side of the stoma receiving opening 32 and downwardly towards a bottom of the appliance 10. Each drainage outlet 41 tapers, i.e. reduces in cross-section, as it extends towards the bottom of the appliance 10.

The distal, lowermost, end of each drainage outlet 41 is moveable relative to the first and second walls 11, 12. Thus, the ends of the drainage outlets 41 are permitted to move freely between the first 11 and second 12 walls of the ostomy appliance 10, which is advantageous, as it will assist in any trapped liquid being shaken into the waste collecting chamber whilst the user is moving around, e.g. walking. Advantageously, the spot welds 93, 94, which are positioned substantially at entrances to the drainage outlets 41, ensure that the walls 13, 14 in that region do not separate from each other, when the bag inflates/fills. This prevents or at least inhibits waste/liquid within the waste collecting chamber 20 from passing into the further chamber 21 through the drainage outlets 41.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. An ostomy appliance including:
first and second walls connected to each other at or near their peripheries defining first and second ends of the appliance having a longitudinal axis extending therethrough, the first wall having a stoma-receiving opening at a first position along the longitudinal axis;
a waste collecting chamber at the second end of the appliance defined by the first and second walls for receiving waste and/or gas from the stoma-receiving opening;
a further chamber having at least a portion at the first end of the appliance and defined by at least third and fourth walls disposed between the first and second walls, wherein the third and fourth walls are coupled to each other, wherein at least a portion of the third wall is coupled to the first wall at a location between the stoma-receiving opening and the periphery of the first wall, and wherein at least a portion of the fourth wall is coupled to the second wall;
a gas opening provided in either or both of the third or fourth walls for permitting waste gases to pass therethrough from the waste collecting chamber to the further chamber;
a gas vent in fluid communication with the further chamber and configured for permitting gases in the further chamber to escape to atmosphere; and
wherein movement of the first and second walls away from each other, as a result of waste or gases entering the waste collecting chamber, increases or at least maintains the volume of the further chamber.

2. An ostomy appliance including:
first and second walls connected to each other at or near their peripheries defining first and second ends of the appliance having a longitudinal axis extending therethrough, the first wall having a stoma-receiving opening at a first position along the longitudinal axis;
a waste collecting chamber at the second end of the appliance defined by the first and second walls for receiving waste and/or gas from the stoma-receiving opening;
a further chamber having at least a portion at the first end of the appliance and defined by at least third and fourth walls disposed between the first and second walls, wherein the third and fourth walls are coupled to each other, wherein at least a portion of the third wall is coupled to the first wall at a location between the stoma-receiving opening and the periphery of the first wall, and wherein at least a portion of the fourth wall is coupled to the second wall;
a gas opening provided in either or both of the third or fourth walls for permitting waste gases to pass therethrough from the waste collecting chamber to the further chamber;
a gas vent in fluid communication with the further chamber and configured for permitting gases in the further chamber to escape to atmosphere; and
wherein movement of the first and second walls away from each other, as a result of waste or gases entering the waste collecting chamber, effects movement of the third and fourth walls away from each other.

3. An ostomy appliance according to claim 2 wherein the further chamber is defined by the third and fourth walls and by one or both of the first or second walls.

4. An ostomy appliance according to claim 2 wherein the third wall is connected to the first wall at a position remote from the peripheral connection of the first and second wall to each other.

5. An ostomy appliance according to claim 2 wherein the fourth wall is connected to the second wall at a position remote from the peripheral connection of the first wall and second wall to each other.

6. An ostomy appliance according to claim 2 wherein the connection of the walls to each other is preferably by way of heat welding.

7. An ostomy appliance according to claim 2 including a plurality of gas openings provided in either or both of the third or fourth walls for permitting waste gases to pass therethrough from the waste collecting chamber.

8. An ostomy appliance according to claim 2 wherein the further chamber is positioned, in use, above the waste collecting chamber.

9. An ostomy appliance according to claim 2 wherein at least a portion of the further chamber is positioned, in use, above the stoma receiving opening.

10. An ostomy appliance according to claim 2 wherein at least a portion of the third wall is connected to the first and second wall at or near the peripheral connection of the first and second walls to each other.

11. An ostomy appliance according to claim 2 wherein the further chamber is at least partially positioned within the waste collecting chamber.

12. An ostomy appliance according to claim 2 wherein the further chamber is positioned within the waste collecting chamber.

13. An ostomy appliance according to claim 2 wherein the fourth wall is connected to the first and second wall at or near the peripheral connection of the first and second walls to each other.

14. An ostomy appliance according to claim 2 wherein the gas vent is covered by a filter.

15. An ostomy appliance according to claim 2 wherein the further chamber is divided into two subchambers by a fifth wall.

16. An ostomy appliance including:
   first and second walls connected to each other at or near their peripheries defining first and second ends of the appliance, the first wall having a stoma-receiving opening;
   a waste collecting chamber at the second end of the appliance defined by the first and second walls for receiving waste and/or gas from the stoma-receiving opening;
   a further chamber having at least a portion at the first end of the appliance and defined by at least third and fourth walls which are connected to each other;
   a gas opening provided in either or both of the third or fourth walls for permitting waste gases to pass therethrough from the waste collecting chamber to the further chamber;
   a gas vent in fluid communication with the further chamber and configured for permitting gases in the further chamber to escape to atmosphere;
   a drainage channel defined by the third and fourth walls, the drainage channel forming a passageway between the further chamber and the waste collecting chamber such that the drainage channel is in fluid communication with the further chamber and the waste collecting chamber for providing a passage for fluid to fall under gravity from the further chamber to the waste collecting chamber, wherein the passageway extends between the first and second ends of the appliance from the further chamber towards the second end, and wherein at least a portion of the third and fourth walls are connected to each other within the passageway; and
   wherein the drainage channel extends to one side of the stoma receiving opening and towards the second end of the appliance.

17. An ostomy appliance according to claim 16 wherein the drainage channel terminates at an opening which is moveable relative to the first and/or second walls.

18. An ostomy appliance according to claim 16 including one or more or all of the following features:
   a) wherein the third and fourth walls are connected to each other at a position above or near an entrance to the drainage channel by a spot or linearly extending weld; and/or
   b) wherein the drainage channel tapers as it extends towards the second end of the appliance; and/or
   c) wherein the appliance includes at least two of said drainage channels one positioned to each side of the stoma receiving opening; and/or
   d) wherein the drainage channel is connected by a wall which extends over the stoma receiving opening.

19. An ostomy appliance according to claim 2 wherein the wall is at least transparent, permitting users to view their stoma therethrough.

20. An ostomy appliance according to claim 2 wherein the ostomy appliance includes an outlet for draining the contents thereof.

21. An ostomy appliance according to claim 1, wherein the third and fourth walls are coupled to each other at a location between the first and second ends of the appliance and at a second position along the longitudinal axis, and wherein the second position is closer to the first end than the first position.

22. An ostomy appliance according to claim 21, wherein at least a portion of the third wall is coupled to the second wall at a location between the stoma receiving opening and the first end.

23. An ostomy appliance according to claim 1, wherein at least a portion of the third wall is coupled to the second wall at a location between the stoma receiving opening and the first end.

* * * * *